United States Patent
Yamabe (10) Patent No.: US 10,226,162 B2
(45) Date of Patent: Mar. 12, 2019

(54) CALIBRATION APPARATUS

(71) Applicant: HOYA CORPORATION, Tokyo (JP)

(72) Inventor: Toshiaki Yamabe, Tokyo (JP)

(73) Assignee: HOYA CORPORATION, Tokyo (JP)

( * ) Notice: Subject to any disclaimer, the term of this patent is extended or adjusted under 35 U.S.C. 154(b) by 1247 days.

(21) Appl. No.: 14/378,487

(22) PCT Filed: Feb. 28, 2013

(86) PCT No.: PCT/JP2013/001249
§ 371 (c)(1),
(2) Date: Aug. 13, 2014

(87) PCT Pub. No.: WO2013/128937
PCT Pub. Date: Sep. 6, 2013

(65) Prior Publication Data
US 2015/0005579 A1    Jan. 1, 2015

(30) Foreign Application Priority Data

Feb. 29, 2012    (JP) ................ 2012-042714

(51) Int. Cl.
*A61B 1/04*    (2006.01)
*A61B 1/00*    (2006.01)
(Continued)

(52) U.S. Cl.
CPC ...... *A61B 1/00057* (2013.01); *A61B 1/00172* (2013.01); *A61B 1/043* (2013.01);
(Continued)

(58) Field of Classification Search
CPC . A61B 1/00057; A61B 1/00172; A61B 1/043; G02B 23/2423; G02B 23/26; G02B 26/101; G02B 26/103
See application file for complete search history.

(56) References Cited

U.S. PATENT DOCUMENTS

2006/0072843 A1 *   4/2006   Johnston .................. G06K 9/20
                                                      382/254
2007/0142707 A1 *   6/2007   Wiklof ............... A61B 1/00096
                                                      600/118
(Continued)

FOREIGN PATENT DOCUMENTS

EP          1805779          7/2007
JP       2008-514342          5/2008
(Continued)

OTHER PUBLICATIONS

Office Action issued in Australia Patent Appl. No. 2013227796, dated Sep. 29, 2016.
(Continued)

*Primary Examiner* — John P Leubecker
*Assistant Examiner* — Arnaldo Torres Diaz
(74) *Attorney, Agent, or Firm* — Greenblum & Bernstein, P.L.C.

(57) ABSTRACT

A calibration apparatus for a scanning endoscope system having a light scanning device configured to cause light emitted from a light source to scan periodically within a predetermined scanning area, comprising: a relay lens to which light emitted from the light scanning device enters and which magnifies the predetermined scanning area; a light detection unit configured to receive light emerging from the relay lens and detect a scanning trajectory of the received light on a light receiving surface of the light detection unit; and a correction unit configured to correct a scanning parameter of the light emitted from the light scanning device so that the scanning trajectory detected by the light detection unit becomes a reference scanning trajectory.

9 Claims, 8 Drawing Sheets

(51) Int. Cl.
   *G02B 23/26* (2006.01)
   *G02B 23/24* (2006.01)
   *G02B 26/10* (2006.01)

(52) U.S. Cl.
   CPC ......... *G02B 23/2423* (2013.01); *G02B 23/26* (2013.01); *G02B 26/103* (2013.01)

(56) References Cited

U.S. PATENT DOCUMENTS

| | | | |
|---|---|---|---|
| 2008/0165360 A1* | 7/2008 | Johnston | A61B 1/00057 356/394 |
| 2009/0026888 A1 | 1/2009 | Melville | |
| 2009/0096994 A1* | 4/2009 | Smits | G02B 26/101 353/30 |
| 2011/0109946 A1* | 5/2011 | Osipchuk | F16F 7/104 358/474 |
| 2011/0249311 A1* | 10/2011 | Engelhardt | G02B 21/0048 359/201.2 |
| 2012/0154784 A1* | 6/2012 | Kaufman | G01B 11/2518 356/4.01 |

FOREIGN PATENT DOCUMENTS

| | | |
|---|---|---|
| JP | 2010-142570 | 7/2010 |
| JP | 2010-534862 | 11/2010 |
| JP | 2011-255015 | 12/2011 |
| WO | 2006/041452 | 4/2006 |

OTHER PUBLICATIONS

European Search Report issued in European Patent Application No. 13755011.7, dated Oct. 19, 2015.
Office Action issued in European Patent Appl. No. 13755011.7, dated Nov. 23, 2016.
International Preliminary Report on Patentability in PCT/JP2013/001249, dated Sep. 12, 2014 (English translation).
International Preliminary Report on Patentability in PCT/JP2013/001249, dated Sep. 2, 2014 (English translation).

\* cited by examiner

CALIBRATION APPARATUS

TECHNICAL FIELD

The present invention relates to a scanning endoscope system having a light scanning device configured to cause light emitted from a light source to scan periodically within a predetermined scanning area, and particularly to a calibration apparatus for the scanning endoscope system configured to correct a scanning trajectory of scanning light.

BACKGROUND ART

Conventionally, a scanning endoscope system configured to cause light guided by an optical fiber to scan in a spiral form with respect to an observation portion, and to image the observation portion by receiving reflected light from the observation portion is known (e.g., Domestic Republication No. JP 2008-514342A1 of PCT international application (hereafter, referred to as "patent document 1")). The scanning endoscope system of this type includes a single mode optical fiber in an endoscope, and a proximal end of the optical fiber is held by a biaxial actuator in a state of a cantilever. The biaxial actuator vibrates (resonate) a tip of the optical fiber in two-dimension in accordance with a characteristic frequency while modulating and amplifying the amplitude of the vibration so that the tip of the optical fiber is driven in a spiral form. As a result, the illumination light guided by the optical fiber from the light source scans on the observation portion in a spiral form, and an image corresponding to an illumination range (a scanning area) is obtained based on returning light from the observation portion.

Recently, it has been proposed that the scanning endoscope system as shown in patent document 1 can be applied to a scanning confocal endoscope system (e.g., Japanese Patent Provisional Publication No. 2011-255015A (hereafter, referred to as "patent document 2")). The scanning confocal endoscope system is configured to emit laser light to a living tissue and to extract only a component, obtained through a pin hole arranged at a position conjugate with a focal point of a confocal optical system, of fluorescence emitted from the living tissue so that observation can be achieved at a magnification higher than that of an observation image obtained by a normal endoscope optical system. The scanning confocal endoscope system described in patent document 2 is configured to be able to observe a minute subject which cannot be observed at a magnification of an observation image obtained by the normal endoscope optical system and to be able to observe a cross section of a living tissue, by scanning in two dimension or three dimension with laser light for a particular narrow area of a living tissue.

In the system described in patent document 1 or 2, reflected light or fluorescence from the scanning area (the observation portion) is received at timings of a predetermined cycle (hereafter referred to as "sampling points"), and intensity information at each sampling point is assigned to a display coordinate of a monitor (a pixel position of an endoscopic image) to display a two-dimensional endoscopic image. Therefore, in order to generate an endoscopic image having a high degree of reproducibility without distortion, it is necessary to set a scanning position of each sampling point to precisely match the display coordinate of the monitor. For this reason, in the scanning endoscope system of this type, calibration is performed while monitoring an actual scanning pattern (scanning trajectory) so as to achieve an ideal scanning pattern (patent document 1).

SUMMARY OF INVENTION

In the scanning endoscope system described in patent document 1, calibration is performed so as to achieve an ideal scanning pattern by receiving illumination light emitted from an optical fiber with a PSD (Position Sensitive Detector), and by adjusting the amplitude, the phase and the frequency of voltages applied to the biaxial actuator while detecting positions of illumination spots in a scanning pattern (scanning trajectory). Such a technique is effective for a scanning endoscope system configured to scan within a relatively wide scanning area (e.g., a scanning area having a diameter of 10 mm), such as a scanning endoscope system described in patent document 1. However, for a scanning confocal endoscope system which scans within a narrow area (e.g., a scanning area having a diameter of 500 µm), such as a scanning confocal endoscope system described in patent document 2, there is a problem that the illumination spot cannot be precisely detected because of limit of resolution of the PSD sensor.

The present invention is made in view of the above described circumstances. That is, the object of the present invention is to provide a calibration apparatus capable of precisely detecting a position of an illumination spot in a scanning pattern and performing calibration to achieve an ideal scanning pattern even if a scanning endoscope system is configured to scan within a narrow scanning area.

To achieve the above described object, a calibration apparatus according to the invention is a calibration apparatus for a scanning endoscope system having a light scanning device configured to cause light emitted from a light source to scan periodically within a predetermined scanning area. The calibration apparatus comprises a relay lens to which light emitted from the light scanning device enters and which magnifies the predetermined scanning area, a light detection unit configured to receive light emerging from the relay lens and detect a scanning trajectory of the received light on a light receiving surface of the light detection unit, and a correction unit configured to correct a scanning parameter of the light emitted from the light scanning device so that the scanning trajectory detected by the light detection unit becomes a reference scanning trajectory.

With this configuration, the scanning trajectory of light emitted from the light scanning device is received on the light detection unit while being magnified to the extent that detection is not affected by the resolution of the light detection unit. Therefore, it is possible to detect the scanning trajectory with a high degree of precision and thereby to perform calibration so that the scanning trajectory becomes an ideal trajectory even if the scanning endoscope system is configured to scan within a narrow scanning area.

The light receiving surface may be arranged to be perpendicular to an optical axis of the relay lens, and a rear focal point of the relay lens may substantially coincide with a center of the light receiving surface.

The calibration apparatus may further comprise a moving unit configured to move the relay lens and the light detection unit relatively with respect to the light scanning device. In this case, the moving unit may move the relay lens and the light detection unit so that a center of the predetermined scanning area substantially coincides with a position of the optical axis of the relay lens, and a position of a front focal point of the relay lens substantially coincides with a convergence point of the light emitted from the light scanning device. With this configuration, the light emitted from the light scanning device is precisely magnified at the magnification of the relay lens. Furthermore, since the light emerging from the relay lens scans the central part of the light detection unit, the light does not deviate from the light receiving surface of the light detection unit.

The relay lens may magnify the predetermined scanning area of the light emitted from the light scanning device so that the predetermined scanning area of the light emerging from the relay lens falls within the light receiving surface.

The scanning parameter may include at least one of a first parameter for magnifying or reducing the predetermined scanning area of scanning light, a second parameter for changing a shape of the predetermined scanning area of the scanning light and a third parameter for changing a scanning speed of the scanning light.

The calibration apparatus may further comprise a remapping table creation unit configured to sample the scanning trajectory of the magnified scanning light corrected by the correction unit at a predetermined timing, and to assign a two dimensional raster coordinate to each sampling point.

The relay lens and the light detection unit may be accommodated in a single case. In this configuration, it is preferable that the case is a blocking case which blocks the light detection unit from external light. With this configuration, it is possible to exclude the effect of the external light. Therefore, it becomes possible to detect the scanning trajectory of the scanning light at a high SN ratio The light scanning device may emit, toward a subject, excitation light having a predetermined wavelength emitted from the light source. The scanning endoscope system may comprise a confocal pinhole arranged at a position conjugate with a convergence point of the excitation light, an image signal detection unit configured to receive fluorescence produced from the subject excited by the excitation light through the confocal pinhole and detects an image signal at a predetermined detection timing, and an image generation unit configured to generate a confocal image using the detected image signal.

According to the calibration apparatus according to the invention, it is possible to precisely detect a position of an illumination spot in a scanning pattern and to perform calibration to achieve an ideal scanning pattern even if a scanning endoscope system is configured to scan within a narrow scanning area.

DESCRIPTION OF EMBODIMENTS

Hereinafter, a scanning confocal endoscope system according to an embodiment of the present invention is described with reference to the accompanying drawings.

Figure 1:
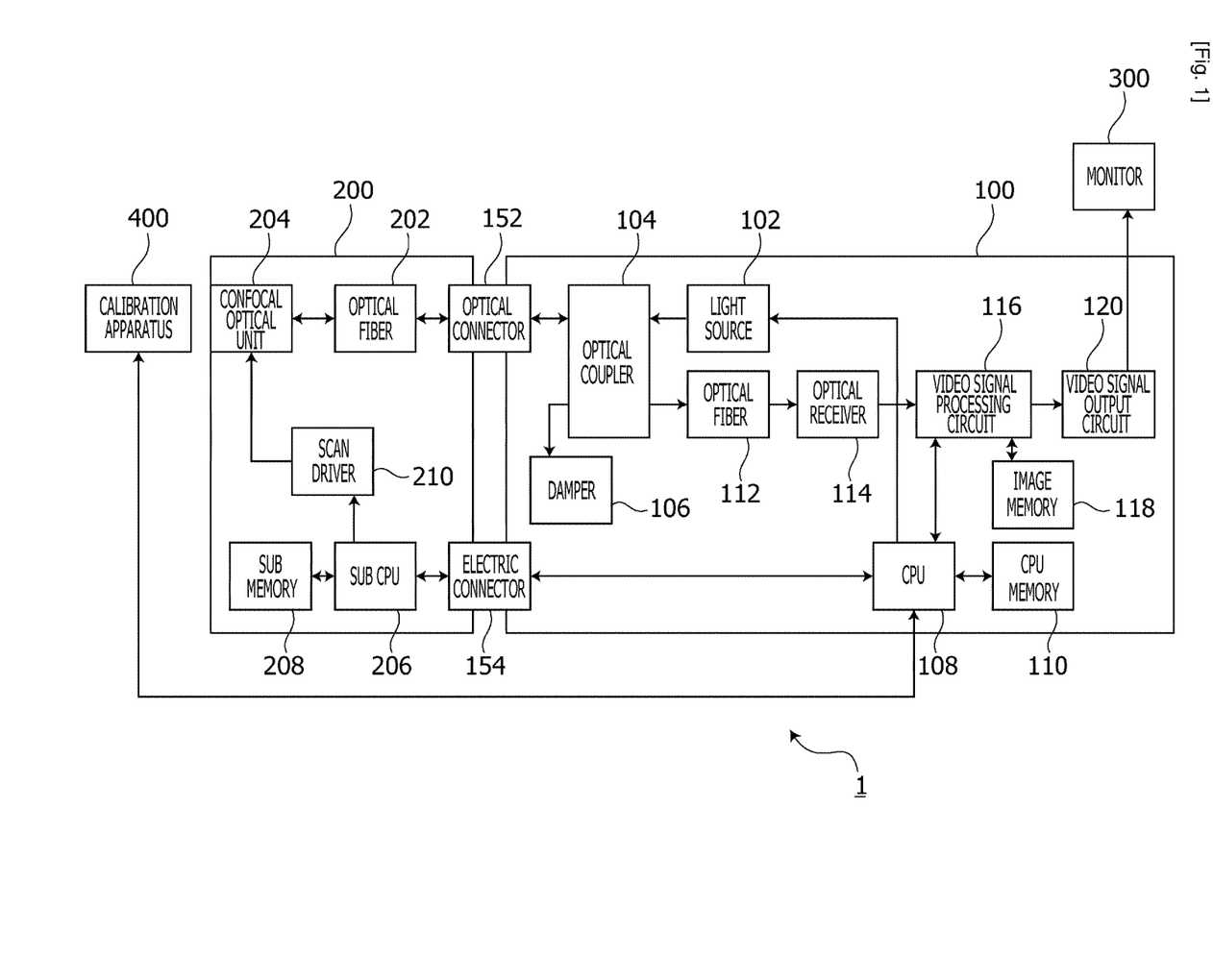
FIG. 1 is a block diagram illustrating a configuration of a scanning confocal endoscope system according to an embodiment of the invention.

The scanning confocal endoscope system is a system designed by making use of a fundamental principle of a confocal microscope, and is configured suitable for observing a subject at a high magnification and a high resolution. FIG. 1 is a block diagram illustrating a configuration of a scanning confocal endoscope system 1 according to the embodiment of the invention. As shown in FIG. 1, the scanning confocal endoscope system 1 includes a system main body 100, a confocal endoscope 200, a monitor 300 and a calibration apparatus 400. Confocal observation using the scanning confocal endoscope system 1 is performed in a state where a tip face of the flexible confocal endoscope 200 having a tube-like shape is operated to contact a subject.

The system main body 100 includes a light source 102, an optical coupler 104, a damper 106, a CPU 108, a CPU memory 110, an optical fiber 112, an optical receiver 114, a video signal processing circuit 116, an image memory 118 and a video signal output circuit 120. The confocal endoscope 200 includes an optical fiber 202, a confocal optical unit 204, a sub CPU 206, a sub memory 208 and a scan driver 210.

The light source 102 emits excitation light which excites medical agents administered in a body cavity of a patient in accordance with driving control by the CPU 108. The excitation light enters the optical coupler 104. To one of ports of the optical coupler 104, an optical connector 152 is coupled. To a non-use port of the optical coupler 104, the damper 106 which terminates, without reflection, the excitation light emitted from the light source 102 is coupled. The excitation light which has entered the former port passes through the optical connector 152, and enters an optical system arranged in the confocal endoscope 200.

A proximal end of the optical fiber 202 is optically coupled to the optical coupler 104 through the optical connector 152. A tip of the optical fiber 202 is accommodated in the confocal optical unit 204 which is installed in a tip portion of the confocal endoscope 200. The excitation light which has exited from the optical coupler 104 enters the proximal end of the optical fiber 202 after passing through the optical connector 152, passes through the optical fiber 202, and thereafter is emitted from the tip of the optical fiber 202

Figure 2:
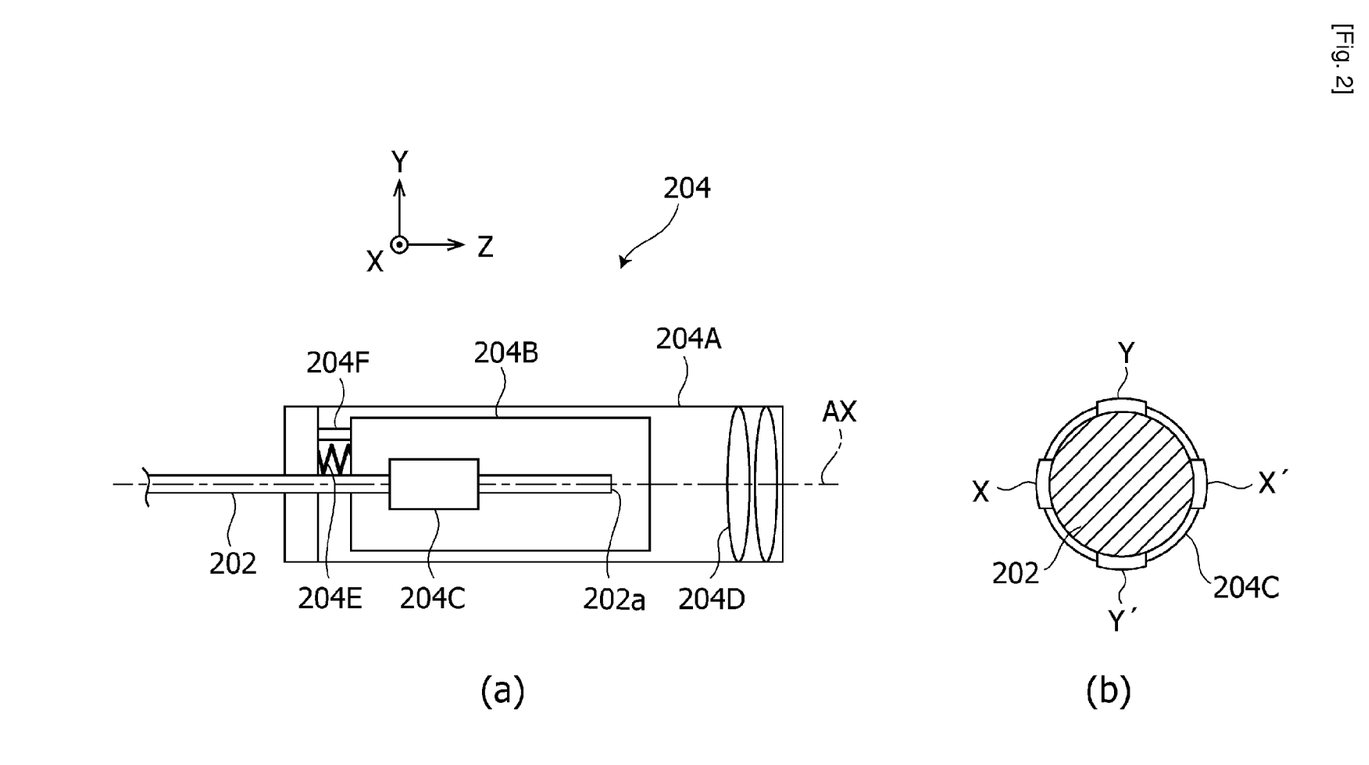
FIG. 2 generally illustrates a configuration of a confocal optical unit included in the scanning confocal endoscope system according to the embodiment of the invention.

FIG. 2 (a) generally illustrates a configuration of the confocal optical unit 204. In the following, for convenience of explanation, a direction of the longer side of the confocal optical unit 204 is defined as Z-direction, and the two directions which are perpendicular to the Z-direction and are perpendicular with respect to each other are defined as X-direction and Y-direction. As shown in FIG. 2(a), the confocal optical unit 204 has a metal outer tube 204A which accommodates various components. The outer tube 204A holds, to be slidable in a coaxial direction, an inner tube 204B having an outer wall shape corresponding to an inner wall shape of the outer tube 204A. The tip (a reference symbol 202a is assigned hereafter) of the optical fiber 202 is accommodated and supported in the inner tube 204B through openings formed in proximal end faces of the outer tube 204A and the inner tube 204B, and functions as a secondary point source of the scanning confocal endoscope system 1. The position of the tip 202a being the point source changes periodically under control by the CPU 108. In FIG. 2(a), the center axis AX represents an axis of the optical fiber 202 arranged in the Z-direction, and when the tip 202a of the optical fiber 202 does not vibrate, the center axis AX coincides with an optical path of the optical fiber 202.

The sub memory 208 stores probe information, such as identification information and various properties of the confocal endoscope 200. The sub CPU 206 reads out the probe information from the sub memory 208 at a time of start-up, and transmits the probe information to the CPU 108 via an electric connector 154 which electrically connects the system main body 100 with the confocal endoscope 200. The CPU 108 stores the transmitted probe information in the CPU memory 110. The CPU 108 generates signals necessary for controlling the confocal endoscope 200 when necessary, and transmits the signals to the sub CPU 206. The sub CPU 206 designates setting values required for the scan driver 210 in accordance with the control signal from the CPU 108.

The scan driver 210 generates a drive signal corresponding to the designated setting value, and drives and controls a biaxial actuator 204C adhered and fixed to the outer surface of the optical fiber 202 close to the tip 202a. FIG. 2(b) generally illustrates a configuration of the biaxial actuator 204C. As shown in FIG. 2(b), the biaxial actuator 204C is a piezoelectric actuator in which a pair of X-axis electrode (X and X' in the figure) and Y-axis electrode (Y and Y' in the figure) connected to the scan driver 210 are formed on a piezoelectric body.

Figure 3:
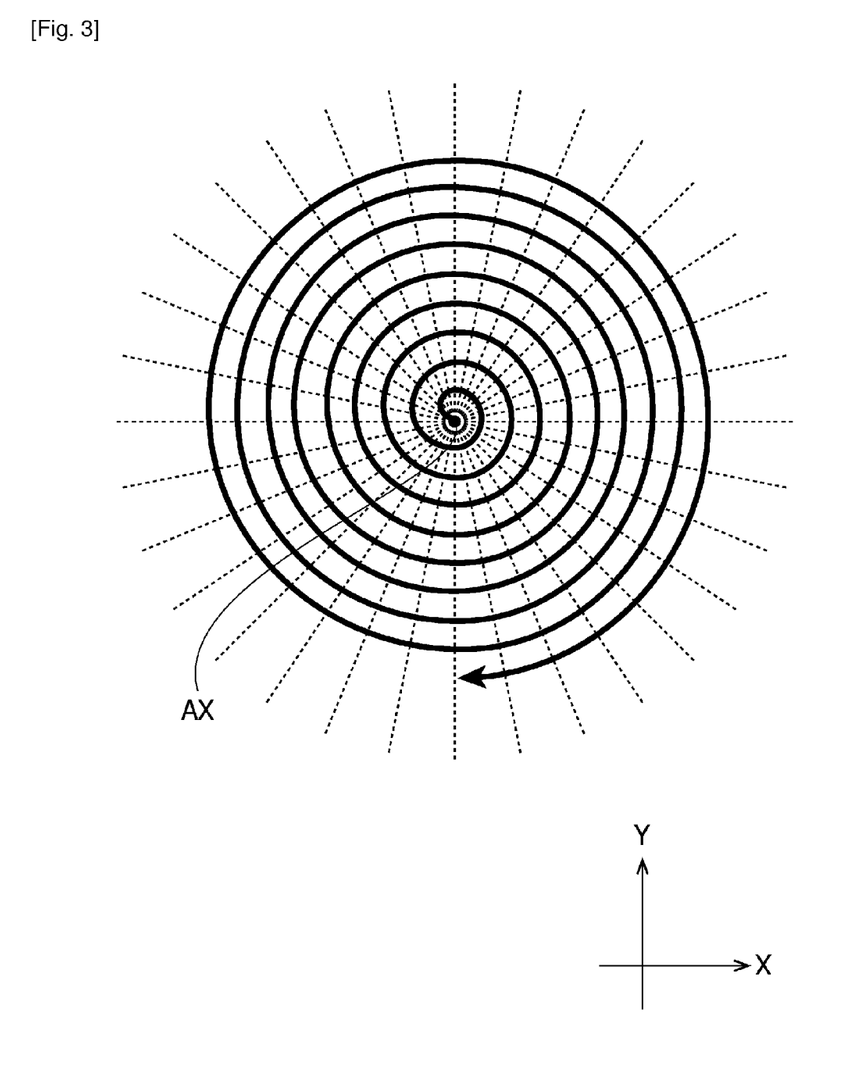
FIG. 3 illustrates a rotational trajectory of a tip of an optical fiber on a XY approximate plane.

The scan driver 210 applies an alternating voltage X between the electrodes for the X-axis of the biaxial actuator 204C so that the piezoelectric body is resonated in the X-direction, and applies an alternating voltage Y which has the same frequency as that of the alternating voltage X and has a phase orthogonal to the phase of the alternating voltage X, between the electrodes for the Y-axis so that the piezoelectric body is resonated in the Y-axis direction. The alternating voltage X and the alternating voltage Y are defined as voltages which linearly increase in amplitude in proportion to time and reach average root-mean-square values (X) and (Y) by taking times (X) and (Y), respectively. The tip 202a of the optical fiber 202 rotates to draw a spiral pattern having the center at the center axis AX on a plane (hereafter, referred to as a "XY approximate plane") which approximates the X-Y plane, due to combining of kinetic energies in the X-direction and Y-direction by the biaxial actuator 204C. A rotation trajectory of the tip 202a becomes larger in proportion to the applied voltage, and becomes a circle having the maximum diameter when the alternating voltages having the average root-mean squares (X) and (Y) are applied. In this embodiment, the amplitudes, the phases and the frequencies of the alternating voltages X and Y are adjusted through calibration which is described later so that the rotation trajectory of the tip 202a becomes an ideal trajectory. FIG. 3 illustrates the rotation trajectory of the tip 202a on the XY approximate plane adjusted through the calibration.

Figure 4:
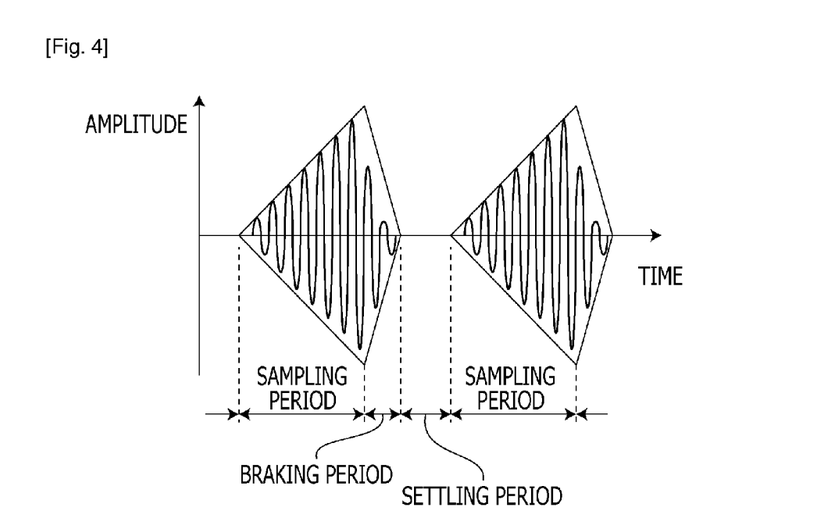
FIG. 4 illustrates a relationship between sampling and braking periods and a changing amount (amplitude) of the tip of the optical fiber in X (or Y) direction on the XY approximate plane.

FIG. 4 illustrates a relationship between various operation timings and the changing amount (amplitude) of the tip 202a of the optical fiber 202 in the X (or Y) direction on the XY approximate plane. The excitation light is continuous light (or pulse light), and is emitted from the tip 202a of the optical fiber 202 during a time period (hereafter, referred to as "sampling period" for convenience of explanation) from start of application of the alternating voltage to the biaxial actuator 204C to stop of application of the alternating voltage. As described above, when the alternating voltage is applied to the biaxial actuator 204C, the excitation light emitted from the tip 202a of the optical fiber 202 scans in a spiral form in a predetermined circular scanning area having the center at the center axis AX because the tip 202a of the optical fiber 202 rotates to draw a spiral pattern having the center at the center axis AX. When application of the alternating voltage to the biaxial actuator 204C is stopped after the sampling period has passed, the vibration of the optical fiber 202 is attenuated. The circular motion of the tip 202a on the XY approximate plane converges in accordance with attenuation of the vibration of the optical fiber 202, and the vibration of the optical fiber 202 becomes almost zero after a predetermined time has passed (i.e., the tip 202a becomes an almost stopped state on the center axis AX). In the following, the time period from an end of the sampling period to the time when the tip 202a becomes an almost stopped state on the center axis AX is referred to as a "braking period" for convenience of explanation. After the braking period has passed and further a predetermined time has passed, a next sampling period is started. In the following, a time period from an end of the braking period to start of the next sampling period is referred to as a "settling period". The settling period is a waiting time for completely stopping the tip 202a of the optical fiber 202 on the center axis AX, and by providing the settling period, it becomes possible to cause the tip 202a to precisely scan. Furthermore, a period corresponding to one frame is formed by one sampling period and one braking period, and by adjusting the settling period, it becomes possible to adjust the frame rate. That is, the settling period can be appropriately set based on the relationship between the frame rate and the time until when the tip 202a of the optical fiber 202 completely stops. To shorten the braking period, a reverse phase voltage may be applied to the biaxial actuator 204C at an initial stage of the braking period so as to positively apply a braking torque.

On the front side of the tip 202a of the optical fiber 202, an objective optical system 204D is arranged. The objective optical system 204D is formed by a plurality of optical lenses, and is held in the outer tube 204A via a lens frame (not shown). The lens frame is fixed and supported relative to the inner tube 204B in the outer tube 204A. Therefore, an optical lens group held on the lens frame slides together with the inner tube 204B in the outer tube 204A. At the forefront of the outer tube 204A (i.e., on the front side of the objective optical system 204D), a cover glass (not shown) is held.

Between a proximal end face of the inner tube 204B and the inner wall of the outer tube 204A, a helical compression spring 204E and a shape memory alloy 204F are attached. The helical compression spring 204E is initially compressed and sandwiched in the Z-direction from a natural length thereof. The shape memory alloy 204F has a rod-like shape elongated in the Z-direction, deforms when an external force is applied thereto under a room temperature condition, and is restored to a predetermined shape by the shape memory effect when heated to be higher than or equal to a predetermined temperature. The shape memory alloy 204F is designed such that the restoring force by the shape memory effect is larger than the restoring force of the helical compression coil 204E. The scan driver 210 generates a driving signal corresponding to the setting value designated by the sub CPU 206, and controls the expanding and contracting amount of the shape memory alloy 204F by electrifying and heating the shape memory alloy 204F. The shape memory alloy 204F causes the inner tube 204B to move forward or backward in the Z-direction in accordance with the expanding and contracting amount.

The excitation light emitted from the tip 202a of the optical fiber 202 forms a spot on a surface or a surface layer of the subject through the objective optical system 204D. A spot formation position moves, in Z-direction, depending on movement of the tip 202a being the point source. That is, the confocal optical unit 204 performs the three dimensional scanning on the subject by combining the periodic circular motion of the tip 202a on the XY approximate plane by the biaxial actuator 204C and the movement in the Z direction.

Since the tip 202a of the optical fiber 202 is arranged at the front focal point of the objective optical system 204D, the tip 202a functions as a pin hole. Of the scattered component (fluorescence) of the subject excited by the excitation light, only fluorescence from the convergence point which is conjugate with the tip 202a is incident on the tip 202a. The fluorescence passes through the optical fiber 202, and then enters the optical coupler 104 through the optical connector 152. The optical coupler 104 separates the entered fluorescence from the excitation light emitted from the light source 102, and guides the fluorescence to the optical fiber 112. The fluorescence is transmitted through the optical fiber 112, and then is detected by the optical receiver 114. In order to detect feeble light with a low level of noise, the optical receiver 114 may be configured as a high-sensitivity optical detector, such as a photomultiplier.

Figure 5:
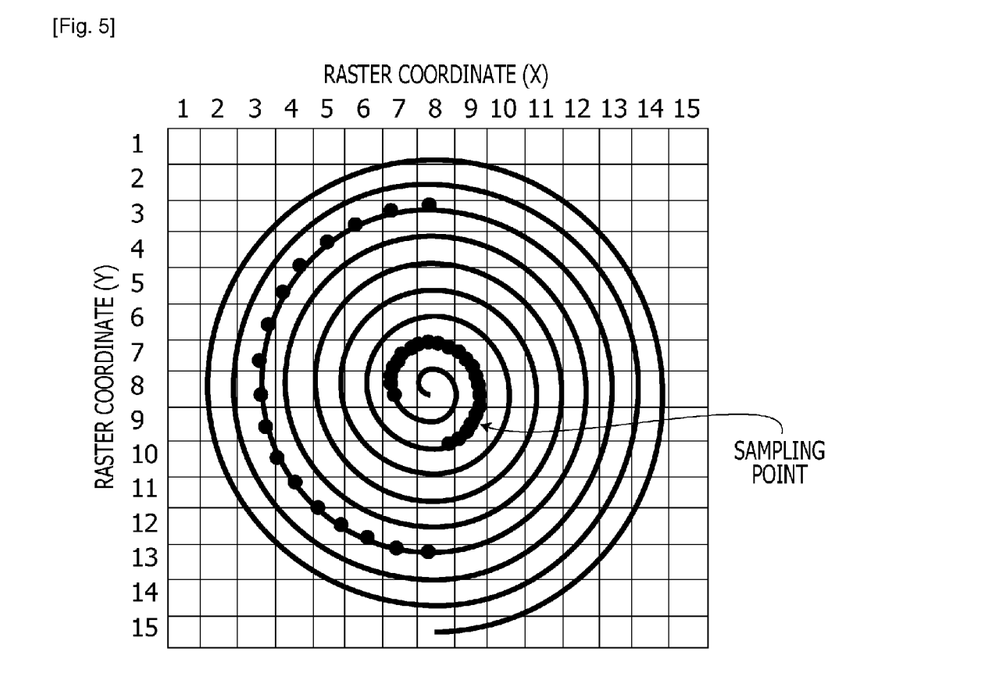
FIG. 5 illustrates a relationship between a sampling point and a raster coordinate.

The detection signal detected by the optical receiver 114 is inputted to the video signal processing circuit 116. The video signal processing circuit 116 operates under control of the CPU 108, and generates a digital detection signal by performing sampling-and-holding and AD conversion for the detection signal at a constant rate. When the position (trajectory) of the tip 202a of the optical fiber 202 during the sampling period is determined, the spot formation position in the observation area (the scanning area) corresponding to the determined position and the signal acquisition timing (i.e., the sampling point) for obtaining the digital detection signal by detecting the returning light (fluorescence) from the spot formation position are definitely defined. As described later, in this embodiment, the scanning trajectory of the tip 202a is measured in advance by using the calibration apparatus 400. Then, the amplitude, the phase and the frequency of the application voltage to the biaxial actuator 204C are adjusted so that the measured scanning trajectory becomes an ideal scanning pattern (i.e., an ideal spiral scanning pattern), and the sampling point and the position (a pixel position of the endoscopic image displayed on the monitor 300) on the image corresponding to the sampling point are determined. The relationship between the sampling point and the pixel position (a pixel address) of the endoscopic image is stored in the CPU memory 110 as a remapping table. For example, if the endoscopic image is formed by 15 pixels in the horizontal direction (X-direction) and 15 pixels in the vertical direction (Y-direction), the relationship between the position (sampling point) of the excitation light sampled sequentially and the pixel position (raster coordinate) of the endoscopic image becomes a state shown in FIG. 5, and the CPU 108 creates the remapping table by obtaining the pixel position (raster coordinate) of the endoscopic image corresponding to each sampling point based on the relationship. In FIG. 5, for convenience of illustration, partial sampling points are shown in the central portion and the peripheral portion of the scanning area; however, actually a number of sampling points exist along the spiral scanning trajectory.

The video signal processing circuit 116 refers to the remapping table, and assigns the digital detection signal obtained at each sampling point as data of a corresponding pixel address. In the following, the above described assigning work is referred to as remapping, for convenience of explanation. The video signal processing circuit 116 performs buffering by storing the signal of the image formed by the spatial arrangement of point images into the image memory 118 on a frame-by-frame manner. The buffered signal is swept out at a predetermined timing from the image memory 118 to the video signal output circuit 120, and is displayed on the monitor 300 after being converted into a video signal complying with a predetermined standard, such as NTSC (National Television System Committee) or PAL (Phase Alternating Line). On a display screen of the monitor 300, a three-dimensional confocal image (which may be simply referred to an "endoscopic image" in this specification) with a high magnification and a high resolution is displayed.

As described above, since the subject image is formed through the remapping operation, the tip 202a needs to be rotated to draw an ideal spiral scanning pattern so that an endoscopic image without distortion can be obtained. However, typically the property of each of the components constituting the scanning confocal endoscope system 1 varies within a certain range. Therefore, it is impossible to obtain an ideal scanning trajectory shown in FIG. 3 if the components are assembled simply. Therefore, in the scanning confocal endoscope system 1 according to the embodiment, the calibration described later is performed to cancel the individual property of the above described type.

Figure 6:
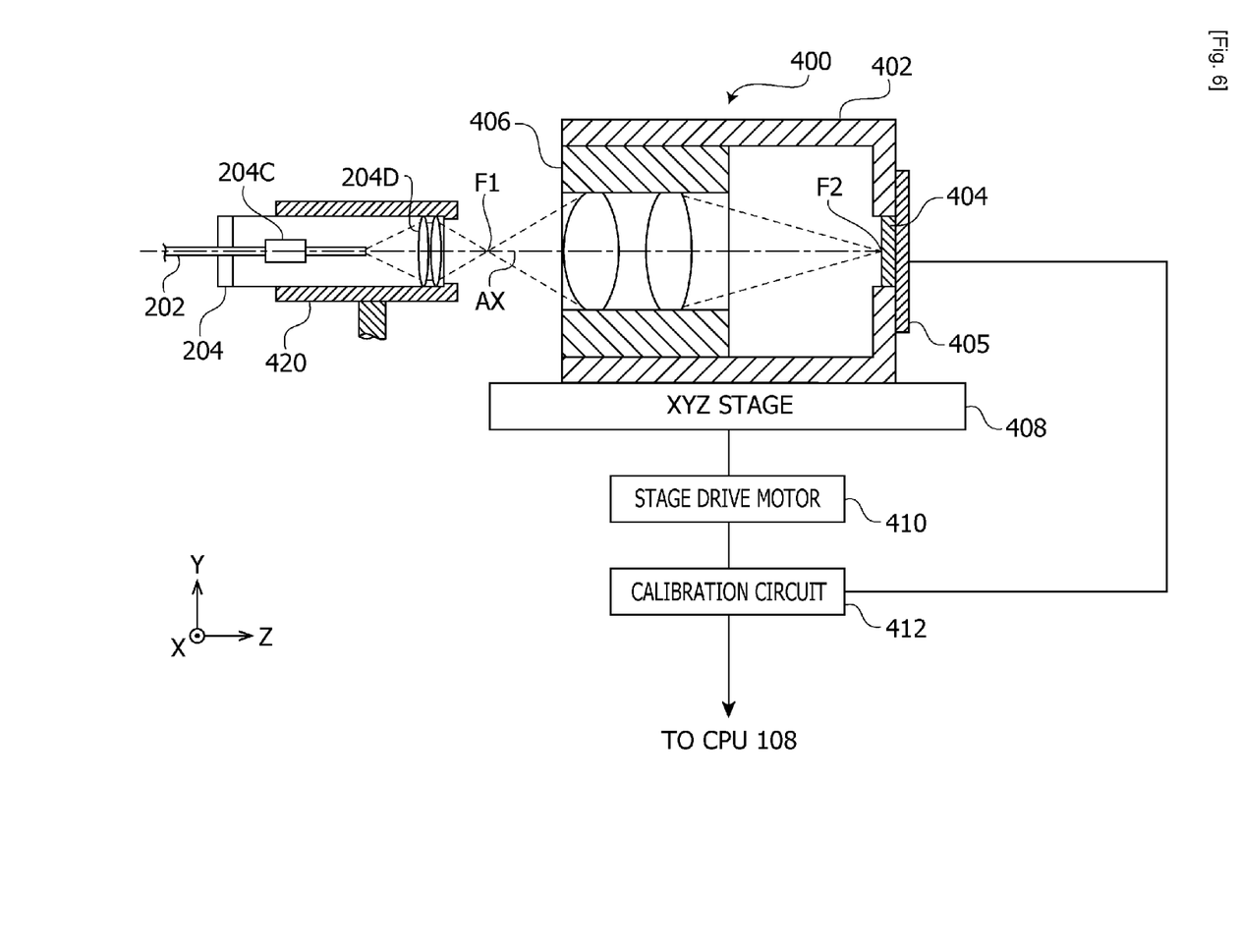
FIG. 6 illustrates a calibration apparatus according to the embodiment of the invention.

FIG. 6 illustrates the calibration apparatus 400 used for the calibration according to the embodiment. In the calibration, a rotational trajectory of the tip 202a of the optical fiber 202 is detected, the amplitude, the phase and the frequency of each of the alternating voltages X and Y to be applied to the biaxial actuator 204C are adjusted so that the rotational trajectory becomes an ideal trajectory (i.e., so that the scanning trajectory of the excitation light emitted from the confocal optical unit 204 becomes a reference scanning trajectory), and a new remapping table is created. In the following, parameters to be adjusted in the calibration, including primarily the amplitude, the phase and the frequency, are collectively referred to as "adjustment parameters". It should be noted that, although the calibration apparatus 400 is explained as a configuration separately provided from the system main body 100, the calibration apparatus 400 may be incorporated in the system main body 100.

As shown in FIG. 6, the calibration apparatus 400 includes a unit support member 420, a case 402, an XYZ stage 408, a stage drive motor 410 and a calibration circuit 412.

The unit support member 420 is a cylindrical member fixed to a main body (not shown) of the calibration apparatus 400, and is configured such that an inner diameter thereof is slightly larger than the outer diameter of the confocal optical unit 204. During the calibration, the confocal optical unit 204 is inserted into the inside of the unit support member 420, and is positioned in X, Y and Z directions.

In the case 402, a PSD 404, a PSD substrate 405 and a relay lens unit 406 are attached. The PSD 404 is mounted on the PSD substrate 405, and is arranged at the proximal side of the case 402 such that a light receiving surface thereof is located in the XY plane (i.e., such that the light receiving surface thereof is perpendicular to the Z direction). The PSD 404 receives the excitation light emitted from the confocal optical unit 204, and detects the position of the excitation light (i.e., the position of the excitation light on the light receiving surface) (details are described later). The relay lens unit 406 is arranged at the tip end side of the case 402 (the confocal optical unit 204 side) so that the optical axis thereof is directed to the Z direction. The relay lens unit 406 is a so-called magnifying optical system including a plurality of lenses therein, and the optical axis and a rear focal point F2 are located at the center of the light receiving surface of the PSD 404. Furthermore, the front focal point F1 of the relay lens unit 406 is adjusted such that the front focal point F1 substantially coincides with the focal point of the objective optical system 204D of the confocal optical unit 204 (i.e., the convergence point of the excitation light). That is, the relay lens unit 406 serves to magnify a projected image at the convergence point of the excitation light emitted from the confocal optical unit 204 (i.e., the scanning area (a maximum swing width) of the excitation light). The magnification of the relay lens unit 406 is determined by totally considering various factors including the size and the position detection resolution of the PSD 404. Assuming a PSD commercially available, it is desirable that, from the position detection resolution thereof, the magnification of the relay lens unit 406 is set so that the size of the scanning range magnified by the relay lens unit 406 has a size larger than or equal to 1 mm on the light receiving surface of the PSD 404, and it is desirable that the magnification of the relay lens unit 406 is set to approximately 2 to 20 magnifications because, from the viewpoints of the device size and the response speed, the magnification of the relay lens unit 406 should be set to be small and it is desirable to use the PSD 404 having a small light receiving surface. For this reason, in this embodiment, the diameter of the scanning area of the excitation light emitted from the confocal optical unit 204 (i.e., the maximum swing width) is set to 500 µm, and the magnification of the relay lens unit 406 is set to be 10 magnifications assuming the size, the position detection resolution and the response speed of a commercially available PSD 404. Therefore, the scanning trajectory of relay lens unit 406, and scans on the light receiving surface of the PSD 404 to draw a circle having the diameter of 5 mm at the maximum. The inside of the case 402 is blocked so as to prevent the external light from entering therein, and the PSD 404 detects the excitation light from the confocal optical unit 204 at a high SN ratio. The detection current of the PSD 404 is outputted to the calibration circuit 412 via the PSD substrate 405.

The case 402 is fixed to the XYZ stage 408 which is movable in the X, Y and Z directions by the stage drive motor 410. The stage drive motor 410 is, for example, a stepping motor, and moves the XYZ stage 408 in a predetermined direction while receiving the signal from the calibration circuit 412. In this embodiment, the movement resolution of the XYZ stage 408 (i.e., the moving amount of the XYZ stage 408 with respect to one step of the stage drive motor 410) is set to approximately 10 µm.

The calibration circuit 412 is a circuit capable of bidirectionally communicating with the CPU 108. Under control of the CPU 108, the calibration circuit 412 moves the XYZ stage 408 through the stage drive motor 410 during the calibration. Furthermore, the calibration circuit 412 converts the detection current of the PSD 404 outputted from the PSD substrate 405 into the voltage, and outputs the voltage to the CPU 108 as the detection voltage.

Figure 7:
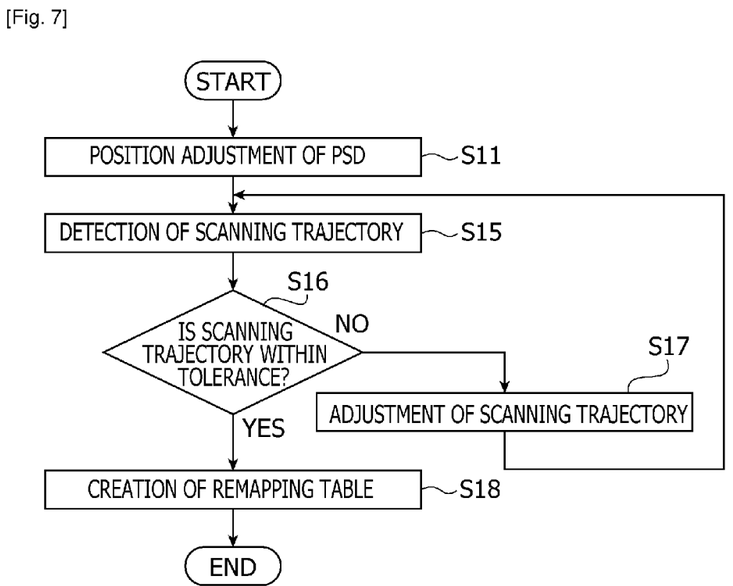
FIG. 7 is a flowchart illustrating a calibration program executed in the scanning confocal endoscope system according to the embodiment of the invention.

FIG. 7 is a flowchart of a calibration program executed during the calibration. The calibration program is a subroutine executed by the CPU 108 when a user (operator) inserts the confocal optical unit 204 into the unit support member 420 and inputs a predetermined command from a user interface (not shown) of the system main body 100. In the explanation of this specification and the drawings, each step of the calibration is abbreviated as "S" for convenience of explanation.

As shown in FIG. 7, when the calibration program is started, the CPU 108 executes S11. At S11, the position of the case 402 is adjusted with respect to the confocal optical unit 204. In this process, the CPU 108 controls the light source 102 so that the excitation light is emitted continuously, and controls the scan driver 210 to stop application of the voltage to the biaxial actuator 204C. As a result, the excitation light emitted from the optical fiber 202 proceeds along the center axis AX, and forms an image on the light receiving surface of the PSD 404 via the relay lens unit 406 (FIG. 6). In this specification, a spot formation position of the excitation light initially defined when no voltage is applied to the biaxial actuator 204C is referred to as an "initial spot formation position".

Figure 8:
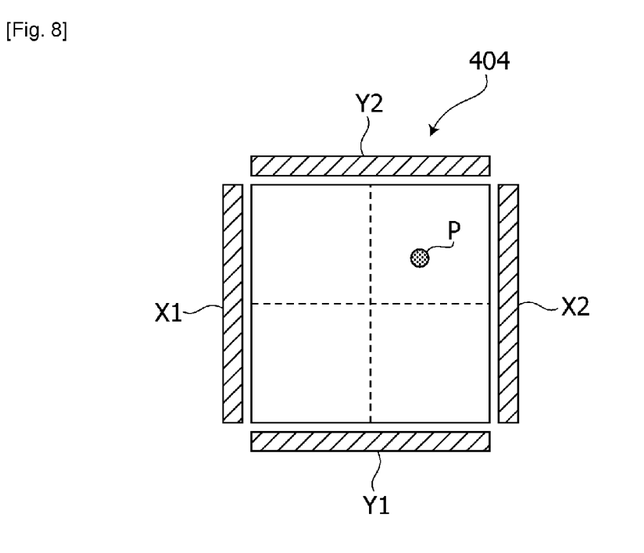
FIG. 8 illustrates an initial spot formation position on a light receiving surface of a PSD.

FIG. 8 illustrates the initial spot formation position P on the light receiving surface of the PSD 404. As described above, since the scanning confocal endoscope system 1 has the individual property, the initial spot formation position does not necessarily coincide with the center of the PSD 404, and is detected at a shifted position in the X and Y directions. The focal point of the objective optical system 204D of the confocal optical unit 204 also varies due to individual differences. Therefore, the front focal point F1 of the relay lens unit 406 does not necessarily coincide with the focal point of the objective optical system 204D of the confocal optical unit 204 (i.e., the convergence point of the excitation light). For this reason, at S11, the case 402 is moved in each of the X and Y directions so that the initial spot formation position substantially coincides with the center of the light receiving surface of the PSD 404 (XY adjustment), and the case 402 is moved in the Z direction so that the front focal point F1 of the relay lens unit 406 substantially coincides with the focal point of the objective optical system 204D of the confocal optical unit 204 (Z adjustment).

(XY Adjustment)

The PSD 404 includes a pair of X direction electrodes X1 and X2 and a pair of Y direction electrodes Y1 and Y2. The spot formation position on the light receiving surface of the PSD 404 is obtained by detecting currents outputted from these electrodes. Specifically, positions Xp, Yp of the initial spot formation position P on the light receiving surface of the PSD 404 is determined by the following expressions (1) and (2).

$$Xp = L \times \frac{I_{X2} - I_{X1}}{I_{X1} + I_{X2}}$$

$$Yp = L \times \frac{I_{Y2} - I_{Y1}}{I_{Y1} + I_{Y2}}$$

In these expressions, $I_{X1}$ represents the current outputted from the electrode X1, $I_{X2}$ represents the current outputted from the electrode X2, $I_{Y1}$ represents the current outputted from the electrode Y1, and $I_{Y2}$ represents the current outputted from the electrode Y2. L represents the distance from the center of the light receiving surface of the PSD 404 and each electrode.

At S11, the CPU 108 obtains the current $I_{X1}$ outputted from the electrode X1, the current $I_{X2}$ outputted from the electrode X2, the current $I_{Y1}$ outputted from the electrode Y1 and the current $I_{Y2}$ outputted from the electrode Y2 from the detected voltage of the PSD 404 inputted from the calibration circuit 412, and obtains the positions Xp, Yp of the initial spot formation position P on the light receiving surface of the PSD 404 based on the above described expressions (1) and (2). Then, the CPU 108 drives the stage drive motor 410 to move the XYZ stage 408 in the X and Y directions so that Xp and Yp take the minimum values (i.e., so that the initial spot formation position substantially coincides with the center of the light receiving surface of the PSD 404). However, as described above, the XYZ stage 408 according to the embodiment has the movement resolution and actually the stage drive motor 410 has backlash, and further these error factors are magnified by the relay lens unit 406. Therefore, it is difficult to make the spot of the excitation light coincide with the center of the light receiving surface of the PSD 404. For this reason, in this embodiment, the PSD 404 having the light receiving surface (10 mm×10 mm) which is sufficiently larger than the scanning area (5 mm×5 mm) of the excitation light on the PSD 404 is used.

Figure 9:
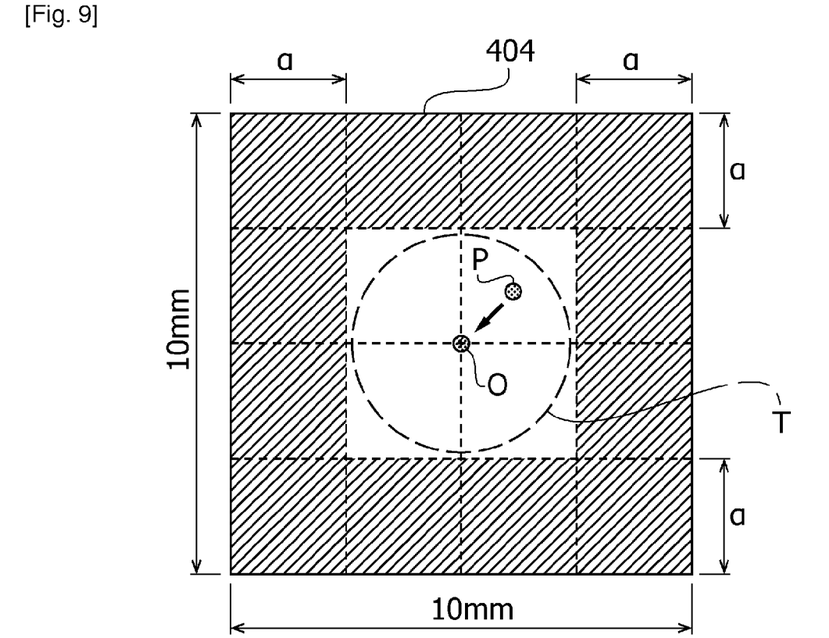
FIG. 9 illustrates a situation where a XY adjustment is performed by the calibration program.

FIG. 9 illustrates the situation where the XY adjustment is performed by S11. In FIG. 9, for convenience of explanation, the situation where the initial spot formation position P has been moved to the center O of the light receiving surface of the PSD 404 is illustrated. When the initial spot formation position P is moved to the center O of the light receiving surface of the PSD 404, the scanning area T of the excitation light becomes an area having a diameter of 5 mm centering at the center O of the light receiving surface. The light receiving surface of the PSD 404 is sufficiently large relative to the scanning area T of the excitation light. A hatched area (an area corresponding to the width of approximately 2.5 mm) surrounding the scanning area T serves as an adjustment margin α for the XY adjustment. That is, even if backlash of the stage drive motor 410 occurs, the scanning area T falls within the light receiving surface of the PSD 404.

(Z Adjustment)

Figure 10:
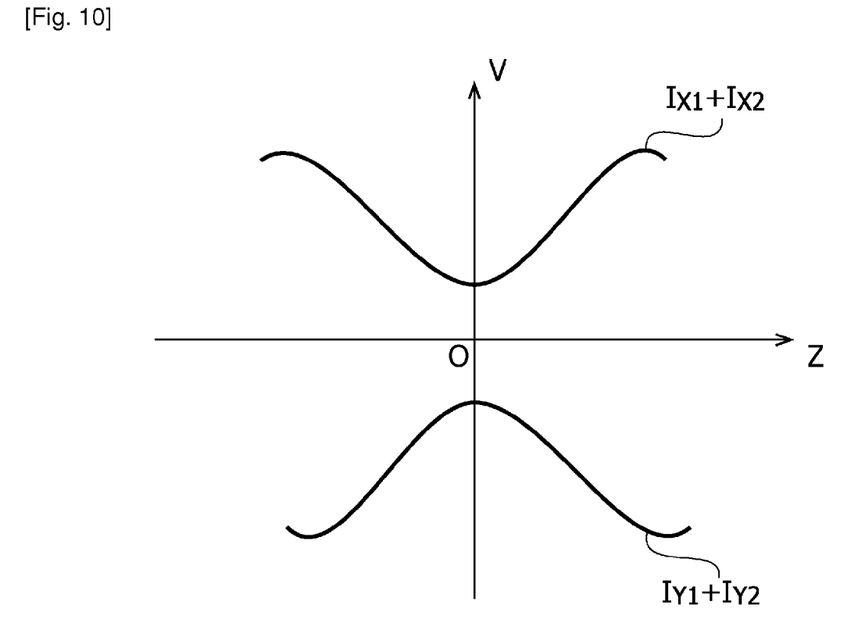
FIG. 10 illustrates a relationship between a moving amount defined when the light receiving surface of the PSD is moved in the Z direction and an output current of the PSD.

FIG. 10 shows the relationship between the moving amount z defined when the light receiving surface of the PSD 404 is moved in the Z direction and the sum $(I_{X1}+I_{X2})$ of the currents in the X direction and the sum $(I_{Y1}+I_{Y2})$ of the currents in the Y direction. In this case, Z=0 is the position defined when the front focal point F1 of the relay lens unit 406 coincides with the focal point of the objective optical system 204D of the confocal optical unit 204. As shown in FIG. 10, when the front focal point F1 of the relay lens unit 406 coincides with the focal point of the objective optical system 204D of the confocal optical unit 204, the excitation light is narrowed most on the light receiving surface of the PSD 404, and the sum $(I_{X1}+I_{X2})$ of the currents in the X direction and the sum $(I_{Y1}+I_{Y2})$ of the currents in the Y direction take extreme values. For this reason, at S11, the Z adjustment is performed by using the sum $(I_{X1}+I_{X2})$ of the currents in the X direction and the sum $(I_{Y1}+I_{Y2})$ of the currents in the Y direction as indicators indicative of the beam diameter of the excitation light. Specifically, the CPU 108 obtains the current $I_{X1}$ outputted from the electrode X1, the current $I_{X2}$ outputted from the electrode X2, the current $I_{Y1}$ outputted from the electrode Y1 and the current $I_{Y2}$ outputted from the electrode Y2 from the detection voltage of the PSD 404 outputted from the calibration circuit 412, and obtains the sum $(I_{X1}+I_{X2})$ of the currents in the X direction and the sum $(I_{Y1}+I_{Y2})$ of the currents in the Y direction. Then, the CPU 108 drives the stage drive motor 410 to move the XYZ stage 408 in the Z direction so that the sum $(I_{X1}+I_{X2})$ of the currents in the X direction and the sum $(I_{Y1}+I_{Y2})$ of the currents in the Y direction take extreme values (i.e., so that the front focal point F1 of the relay lens unit 406 substantially coincides with the focal point of the objective optical system 204D of the confocal optical unit 204).

As described above, at S11, the XY adjustment where the case 402 is moved in each of the X and Y directions and the Z adjustment where the case 402 is moved in the Z direction are performed, so that the initial spot formation position substantially coincides with the center of the light receiving surface of the PSD 404 and the front focal point F1 of the relay lens unit 406 substantially coincides with the focal point of the objective optical system 204D of the confocal optical unit 204. In the forgoing, for convenience of explanation, explanation is given in order of the XY adjustment and the Z adjustment; however, the adjustment may be performed in order of the Z adjustment and the XY adjustment. When the Z adjustment is performed prior to the XY adjustment, the XY adjustment can be performed in the state where the spot of the excitation light is narrowed. Therefore, the XY adjustment becomes hard to be affected by the aberrations of the objective optical system 204D and the relay lens unit 406, inclination of the objective optical system 204D and an installation error of the confocal optical unit 204, and the XY adjustment can be performed with a high degree of precision. Then, the process proceeds to S15 (FIG. 7).

Figure 11:
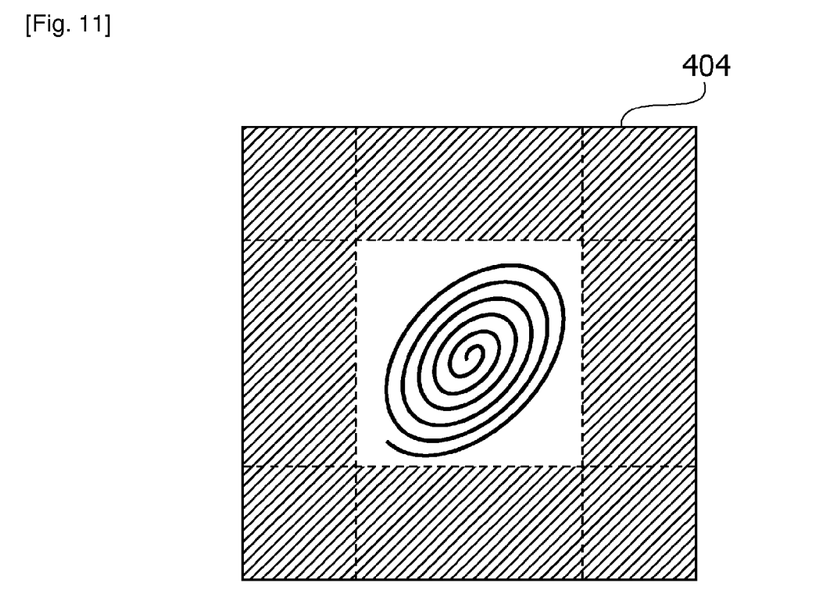
FIG. 11 illustrates a scanning trajectory of excitation light defined when predetermined X and Y alternating voltages are applied to a biaxial actuator.

At S15, the CPU 108 applies default alternating voltages X and Y to the biaxial actuator 204C to rotate the tip 202a of the optical fiber 202, and detects a scanning trajectory of the excitation light which spirally scans on the light receiving surface of the PSD 404. FIG. 11 illustrates a scanning trajectory of the excitation light defined when the default alternating voltages X and Y are applied to the biaxial actuator 204C. Since, as described above, the scanning confocal endoscope system 1 has the product individual property, the ideal scanning trajectory such as shown in FIG. 3 cannot be achieved in the state where the default alternating voltages X and Y are applied, and in this case the scanning trajectory takes, for example, an elliptically deformed shape. Then, the process proceeds to S16.

At S16, the CPU 108 evaluates the scanning trajectory of the excitation light detected at S15, and judges whether the scanning trajectory is within a predetermined tolerance (i.e., whether the scanning trajectory is an acceptable scanning trajectory). The predetermined tolerance is determined in advance based on the amount of distortion of an acceptable image. The CPU 108 evaluates the size, the shape (circularity) and the scanning speed of the scanning area from the scanning trajectory of the excitation light detected at S15. When it is judged that the scanning trajectory is within the predetermined tolerance at S16 (S16: YES), the process proceeds to S18. When it is judged that the scanning trajectory is not within the predetermined tolerance (S16: NO), the process proceeds to S17.

Figure 12:
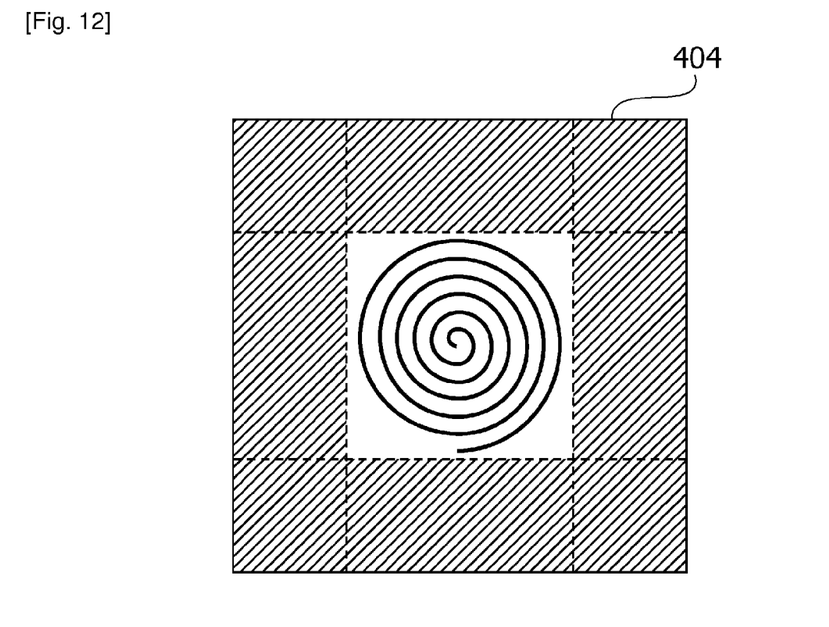
FIG. 12 illustrates a scanning trajectory of the excitation light defined when the scanning trajectory is adjusted by the calibration to be an ideal scanning trajectory.

At S17, the CPU 108 alters the adjustment parameters of the alternating voltages X and Y to be applied to the biaxial actuator 204C. Specifically, based on the evaluation result of the scanning trajectory of the excitation light at S16, the CPU 108 adjusts the amplitudes of the alternating voltages X and Y to magnify or reduce the scanning area when there is a problem with the size of the scanning area. When there is a problem with the shape of the scanning area, the CPU 108 adjusts the phases of the alternating voltages X and Y to alter the shape of the scanning area. When there is a problem with the scanning speed of the scanning area, the CPU 108 adjusts the frequencies of the alternating voltages X and Y to change the scanning speed of the excitation light. The CPU 108 repeatedly executes steps to S15 to S17 until the scanning trajectory is within the tolerance. As a result, the scanning trajectory of the excitation light detected at S15 is adjusted so as to be the ideal scanning trajectory shown in FIG. 12.

At S18, the CPU 108 obtains the relationship between each sampling point and the pixel position (pixel address) of the endoscopic image for the scanning trajectory adjusted at S17, and creates a new remapping table. Then, the CPU 108 stores the created remapping table in the CPU memory 110 together with the adjustment parameters adjusted at S17 (i.e., the amplitudes, the phases and the frequencies of the alternating voltages X and Y), and then terminates the calibration program. The remapping table and the adjustment parameters stored in the CPU memory 110 at S18 are repeatedly used until new calibration is executed.

As described above, in the calibration according to the embodiment, the scanning trajectory of the excitation light emitted from the confocal optical unit 204 is magnified by the relay lens unit 406 and is received by the PSD 404. That is, the scanning trajectory of the excitation light emitted from the confocal optical unit 204 is magnified to the extent that the scanning trajectory is not affected by the resolution on the PSD 404. Therefore, even if a scanning endoscope system configured to scan within a narrow scanning area, such as the scanning confocal endoscope system 1 according to the embodiment is used, it is possible to detect the scanning trajectory with a high degree of precision and thereby it becomes possible to perform calibration (adjustment) to achieve the ideal scanning trajectory.

The foregoing is the explanation of the embodiment of the present invention; however, the invention is not limited to the above described embodiment, but can be varied in various ways within the scope of the technical concept of the invention. For example, in the above described embodiment, it is explained that the CPU 108 executes the calibration program; however, the present invention is not limited to the above described embodiment. The calibration program may be executed by the calibration circuit 412. In this case, the calibration circuit 412 is configured to control the biaxial actuator 204C and change the adjustment parameters through communication with the CPU 108.

At S11 of the calibration program according to the embodiment, the XY adjustment and the Z adjustment are performed in the state where the rotational driving of the optical fiber 202 is stopped. However, the XY adjustment and the Z adjustment can be performed even when the optical fiber 202 is in the state of being rotationally driven, by detecting the spot position of the excitation light during the braking period.

In the above described embodiment, the PSD 404 having the sufficiently wide light receiving surface with respect to the scanning area of the excitation light on the PSD 404 is used considering the movement resolution of the XYZ stage 408 and the backlash of the stage drive motor 410. However, by configuring the calibration apparatus 400 such that the movement resolution of the XYZ stage 408 and the backlash of the stage drive motor 410 become small, it becomes possible to further magnify the scanning area of the excitation light on the PSD 404.

The magnification of the relay lens unit 406 according to the embodiment is 10 magnifications. However, as described above, the magnification of the relay lens unit 406 may be set to approximately 2 to 20 magnifications, and by magnifying the scanning area of the excitation light on the PSD 404 to the extent that the scanning area falls within the light receiving surface of the PSD 404, it becomes possible to more precisely detect the scanning trajectory of the excitation light.

A system to which the present invention is applied is not limited to a scanning confocal endoscope system. It is sufficient that the PSD 404 receives light within the scanning area magnified by the relay lens unit 406, and therefore the present invention can be applied to a general scanning endoscope system. For example, the present invention may be applied to a scanning endoscope system employing a raster scanning manner in which light horizontally scans on a scanning area to reciprocate or a Lissajous scanning manner in which light sinusoidally scans on a scanning area.

In the above described embodiment, the confocal optical unit 204 is installed in the tip of the confocal endoscope 200. However, the confocal optical unit 204 may be installed in a confocal probe inserted into an instrument insertion channel of an endoscope.

A position detection device to be installed in the calibration apparatus 400 is not limited to a PSD. The PSD 404 may be replaced with another device which is able to detect the position and the light amount, such as a CCD (Charge Coupled Device) and an array type PMT (Photomultiplier Tube).

The invention claimed is:

1. A calibration apparatus for a scanning endoscope system having a light scanning device, including an actuator, that causes light emitted from a light source to scan periodically within a predetermined scanning area, the calibration apparatus comprising:
a relay lens to which light emitted from the light scanning device enters and which magnifies the predetermined scanning area;
a position sensitive detector that receives light emerging from the relay lens and detects a scanning trajectory of the received light on a light receiving surface of the position sensitive detector;
a processor that corrects a scanning parameter of the light emitted from the light scanning device so that the scanning trajectory detected by the position sensitive detector becomes a reference scanning trajectory; and
a moving unit, including a motor, that moves the relay lens and the position sensitive detector relatively with respect to the light scanning device,
wherein the processor causes the moving unit to move the relay lens and the position sensitive detector so that a center of the predetermined scanning area substantially coincides with a position of an optical axis of the relay lens, and a position of a front focal point of the relay lens substantially coincides with a convergence point of the light emitted from the light scanning device.

2. The calibration apparatus according to claim 1,
wherein:
the light receiving surface is arranged to be perpendicular to the optical axis of the relay lens; and
a rear focal point of the relay lens substantially coincides with a center of the light receiving surface.

3. The calibration apparatus according to claim 2,
wherein the relay lens magnifies the predetermined scanning area of the light emitted from the light scanning device so that the predetermined scanning area of the light emerging from the relay lens falls within the light receiving surface.

4. The calibration apparatus according to claim 1,
wherein:
the position sensitive detector detects a position and a beam diameter of the light on the optical axis of the relay lens; and
the processor causes the moving unit to move the relay lens and the position sensitive detector so that the position of the light on the optical axis of the relay lens substantially coincides with the center of the light receiving surface, and that the beam diameter takes a minimum value.

5. The calibration apparatus according to claim 1,
wherein the scanning parameter includes at least one of a first parameter for magnifying or reducing the predetermined scanning area of scanning light, a second parameter for changing a shape of the predetermined scanning area of the scanning light and a third parameter for changing a scanning speed of the scanning light.

6. The calibration apparatus according to claim 1, wherein
the processor further samples the scanning trajectory of the magnified scanning light corrected by the processor at a predetermined timing, and assigns a two dimensional raster coordinate to each sampling point.

7. The calibration apparatus according to claim 1,
wherein the relay lens and the position sensitive detector are accommodated in a single case.

8. The calibration apparatus according to claim 7,
wherein the case is a blocking case which blocks the position sensitive detector from external light.

9. The calibration apparatus according to claim 1,
wherein the light scanning device emits, toward a subject, excitation light having a predetermined wavelength emitted from the light source, and
wherein the scanning endoscope system comprises:
a confocal pinhole arranged at a position conjugate with a convergence point of the excitation light;
an optical detector that receives fluorescence produced from the subject excited by the excitation light through the confocal pinhole and detects an image signal at a predetermined detection timing; and
a processor that generates a confocal image using the detected image signal.

* * * * *